US010015965B2

(12) United States Patent
Buttimor

(10) Patent No.: US 10,015,965 B2
(45) Date of Patent: *Jul. 10, 2018

(54) METHODS FOR USING STABLE SOLID HERBICIDE DELIVERY SYSTEMS

(71) Applicant: DOW AGROSCIENCES LLC, Indianapolis, IN (US)

(72) Inventor: Robert Buttimor, New Plymouth (NZ)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/117,762

(22) PCT Filed: Feb. 9, 2015

(86) PCT No.: PCT/NZ2015/050009
§ 371 (c)(1),
(2) Date: Aug. 10, 2016

(87) PCT Pub. No.: WO2015/119513
PCT Pub. Date: Aug. 13, 2015

(65) Prior Publication Data
US 2016/0360750 A1    Dec. 15, 2016

(30) Foreign Application Priority Data

Feb. 10, 2014   (NZ) .................................... 621068

(51) Int. Cl.
*A01N 43/40* (2006.01)
*A01N 25/08* (2006.01)
*A01N 25/12* (2006.01)
*A01N 25/26* (2006.01)

(52) U.S. Cl.
CPC ............. *A01N 43/40* (2013.01); *A01N 25/08* (2013.01); *A01N 25/12* (2013.01); *A01N 25/26* (2013.01)

(58) Field of Classification Search
None
See application file for complete search history.

(56) References Cited

U.S. PATENT DOCUMENTS

| 3,940,260 | A | * | 2/1976 | Kauffman | A01N 37/02 504/145 |
|---|---|---|---|---|---|
| 6,579,831 | B1 | | 6/2003 | Harwell | |
| 8,163,672 | B2 | | 4/2012 | Birthisel | |
| 2007/0072775 | A1 | | 3/2007 | van Boxtel-Verhoeven et al. | |
| 2010/0105558 | A1 | | 4/2010 | Li et al. | |
| 2011/0287935 | A1 | | 11/2011 | Patzoldt et al. | |
| 2012/0015811 | A1 | | 1/2012 | Dave et al. | |
| 2012/0149572 | A1 | | 6/2012 | Gewehr et al. | |
| 2013/0190176 | A1 | | 7/2013 | Dave et al. | |
| 2014/0031214 | A1 | * | 1/2014 | Yerkes | A01N 43/40 504/103 |
| 2014/0162878 | A1 | * | 6/2014 | Ovalle | A01N 43/54 504/239 |

FOREIGN PATENT DOCUMENTS

| WO | 2011/069890 A2 | 6/2011 |
| WO | 2014/093210 A1 | 6/2014 |
| WO | 2014/202092 A1 | 12/2014 |

OTHER PUBLICATIONS

International Search Report and Written Opinion of the International Searching Authority for International Application No. PCT/NZ2015/050010, dated May 19, 2015, 11 pages.
Non-Final Office Action dated Jul. 26, 2017 in related U.S. Appl. No. 15/117,768 (17 pages).
VICAL 1000, by Mineral Technologies Inc, 2014.
International Search Report and Written Opinion of the International Searching Authority for International Application No. PCT/NZ2015/050009, dated May 19, 2015, 11 pages.

* cited by examiner

*Primary Examiner* — Alton N Pryor
(74) *Attorney, Agent, or Firm* — Michael R. Asam; Meunier Carlin & Curfman, LLC

(57) ABSTRACT

Methods of controlling undesirable vegetation comprising contacting the vegetation or the locus thereof with, or applying to the soil to control or prevent the emergence of the vegetation, a herbicidally effective amount of a herbicide delivery system.

12 Claims, No Drawings

METHODS FOR USING STABLE SOLID HERBICIDE DELIVERY SYSTEMS

CROSS-REFERENCE TO RELATED APPLICATIONS

This application is a national stage application filed under 35 U.S.C. § 371 of PCT/NZ2015/050009 filed Feb. 9, 2015, which claims the benefit of and priority to New Zealand Patent Application No. 621068 filed on Feb. 10, 2014, the disclosures of which are expressly incorporated herein by reference in their entireties.

BACKGROUND

Compositions containing herbicidal and plant growth modifying chemicals are widely used in agricultural, industrial, recreational, and residential areas worldwide. The active ingredients of such compositions are frequently carboxylic acids, more particularly their salts. These carboxylic acid salts generally have very high water solubility leading to their use in aqueous concentrates intended for dilution in water prior to application by spraying and also in granules for non-spray, broadcast application.

Granule (GR) products for non-spray, broadcast application may be used for insect, weed, fungal pathogen and nematode control and are often used in soil and aquatic environments. Because of the particle weight, granules used in aerial applications may pose a reduced hazard from off-target drift compared to aerial liquid spray applications.

In some situations, granule compositions containing salts of herbicidal carboxylic acids require additional processing steps in order to improve their storage stability. Such compositions may require the use of a final surface coating step and an additional drying step in order to prevent stickiness and caking of the granules.

SUMMARY

Provided herein are methods of controlling undesirable vegetation. The methods of controlling undesirable vegetation include contacting the vegetation or the locus thereof with, or applying to the soil to control or prevent the emergence of the vegetation, a herbicidally effective amount of a herbicide delivery system comprising a solid carrier and a potassium salt of a herbicidal carboxylic acid coated onto the surface of the solid carrier, wherein the potassium salt of the herbicidal carboxylic acid is from about 0.1 gram acid equivalent per kilogram (g ae/kg) to about 100 g ae/kg of the total herbicide delivery system and the coated solid carrier is free flowing and does not cake during storage.

DETAILED DESCRIPTION

Described herein are methods of controlling undesirable vegetation comprising contacting the vegetation or the locus thereof with, or applying to the soil to control or prevent the emergence of the vegetation, a herbicidally effective amount of a herbicide delivery system. The herbicide delivery system used in the methods comprises a potassium salt of a herbicidal carboxylic acid coated onto a solid carrier. Compositions, where the potassium salt of the herbicidal carboxylic acid is applied to the surface of the solid carrier to form coated granules, have excellent storage stability, can be produced in a simple and cost effective manner, and offer acceptable herbicidal efficacy when used to control weeds in non-spray, broadcast or spot applications.

The herbicide delivery system described herein includes:
a) a solid carrier;
b) a potassium salt of a herbicidal carboxylic acid coated onto the surface of the solid carrier; and
c) optionally, one or more inert formulation ingredients.

The potassium salt of the herbicidal carboxylic acid coated onto the solid carrier comprises from about 0.1 gram acid equivalent per kilogram (g ae/kg) to about 100 g ae/kg of the total weight of the herbicide delivery system. The herbicide delivery system described herein can be in the form of broadcast-type granules that are coated with one or more of a potassium salt of a herbicidal carboxylic acid. The coated granules of the herbicide delivery system described herein are free-flowing and do not cake during storage.

Solid carriers in the form of granules that are suitable for use in the described herbicide delivery system can be broadly separated into two categories: inorganic and organic. Inorganic granular carriers include, for example, silicas and silicates, such as sand, talc (hydrated magnesium silicate), palygorskites, pyrophyllites, attapulgus clay, kaolinite clay, bentonite clay, montmorillonite clay, illite clay and Fuller's earth; diatomaceous earths such as diatomite, tripolite and kieselgur/kieselguhr; carbonate chemicals or minerals such as calcium carbonate (e.g., limestone, calcite, and chalk), and calcium magnesium carbonate (Dolomite); sulfates such as calcium sulfate (gypsum); chlorides such as potassium chloride; oxides such as calcium oxide and magnesium oxide; phosphate minerals such as the apatites; elemental materials such as sulfur; and volcanic materials such as pumice. Also, some inorganic granular solid carriers can be synthetically prepared from mineral materials, such as precipitated hydrated calcium silicate, precipitated calcium carbonate, and precipitated hydrated silicon dioxide. Organic granular carriers may include, for example, corn cobs, pecan shells, peanut hulls, cottonseed hulls, wheat flour, soybean flour, wood flour, walnut shell flour, lignin, citrus pulp, corn cobs, ground grains, rice hulls, soybeans, tobacco, walnut shells, and wood recycled paper fiber, etc. In its simplest form, a granular formulation consists of the inert granule and the pesticide. The solid carrier may have a specific carrying capacity for the pesticide and any additional inert ingredients. Such a carrying capacity can be adsorptive and/or absorptive in nature and is generally dependent on the composition of the solid carrier. The solid carrier will normally be selected based on the particular application needs for the herbicide delivery system. The solid carriers described herein are in the form of granules that range in size from about 100 to about 5000 microns (μm), from about 200 to about 4000 μm, from about 300 to about 3000 μm, from about 350 to about 2000 μm, from about 350 to about 1500 μm, from about 400 to about 1300 μm, or from about 400 to about 1200 μm.

In some embodiments, the solid carrier for use in the described herbicide delivery system is comprised of mineral derived inorganic granules that have a particle size range from about 100 to about 5000 μm.

In some embodiments, the solid carrier for use in the described herbicide delivery system is comprised of limestone chips (i.e., granules) that have a hard inert surface, are irregular in shape, and have a particle size range from about 400 μm to about 1200 μm, where greater than about 80% of the chips have a particle size within this range.

The potassium salt of a herbicidal carboxylic acid to be coated onto the surface of the solid carrier, e.g., granule, may be melted into a liquid, dissolved in a solvent or dispersed in a liquid, which may then be sprayed onto the granule. In the absence of effective ingredients, dry granules may be physically unstable and slowly breakdown forming a dust or powder. In some cases, granules containing pesticide ingredients may stick together, e.g. cake, which can negatively impact their handling properties and performance. In some cases the stickiness of the granules can be inhibited or prevented by the use of anti-caking additives and/or by application of an anti-sticking coating to the surface of the coated granule.

Using the systems and methods described herein, potassium salts of herbicidal carboxylic acids in the form of solids or liquids that are to be coated onto the surface of the solid carrier may be formulated as broadcast-type granules. Such herbicide delivery system granule formulations usually contain a relatively small amount of the pesticide ingredient since the granules are frequently not further diluted with a carrier solvent such as water prior to use, but are instead applied by placement or broadcast of the granules directly onto the area of interest, such as for example, plant vegetation, soil or water. Once applied, the active ingredient contained in the herbicide delivery system is released to the area of application, typically upon exposure to water.

The herbicidal carboxylic acids useful in the herbicide delivery system described herein include aryl- or heteroaryl carboxylic acid compounds of the following general formula

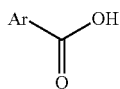

wherein Ar is a phenyl, pyridine, pyrimidine or quinoline group substituted with one or more substituents selected from halogen, $C_1$-$C_6$ alkyl, $C_1$-$C_6$ haloalkyl, $C_1$-$C_6$ alkoxy, amino, $C_1$-$C_6$ alkylamino, and di($C_1$-$C_6$ alkyl)amino. Suitable herbicidal carboxylic acids for use in the described herbicide delivery system may include aminopyralid, aminocyclopyrachlor, clopyralid, dicamba, picloram, and mixtures thereof.

In some embodiments, the herbicidal carboxylic acid for use in the herbicide delivery system described herein is picloram.

In some embodiments, the herbicidal carboxylic acids for use in the herbicide delivery system described herein are a mixture of picloram and aminopyralid.

The herbicidal carboxylic acids described herein comprise, with respect to the total herbicide delivery system, from about 0.1 g ae/kg to about 100 g ae/kg, 0.1 g ae/kg to about 80 g ae/kg, 0.1 g ae/kg to about 60 g ae/kg, 0.1 g ae/kg to about 50 g ae/kg, 0.1 g ae/kg to about 40 g ae/kg, 0.1 g ae/kg to about 30 g ae/kg, 0.1 g ae/kg to about 25 g ae/kg, 0.1 g ae/kg to about 20 g ae/kg, 0.1 g ae/kg to about 15 g ae/kg, 0.1 g ae/kg to about 10 g ae/kg, 0.1 g ae/kg to about 8 g ae/kg, 0.1 g ae/kg to about 6 g ae/kg, 0.1 g ae/kg to about 4 g ae/kg, 0.1 g ae/kg to about 2 g ae/kg, or 0.1 g ae/kg to about 1 g ae/kg. The herbicidal carboxylic acids described herein may also comprise from about 1 g ae/kg to about 100 g ae/kg, 2 g ae/kg to about 80 g ae/kg, 4 g ae/kg to about 80 g ae/kg, 6 g ae/kg to about 70 g ae/kg, 8 g ae/kg to about 70 g ae/kg, 10 g ae/kg to about 70 g ae/kg, 10 g ae/kg to about 60 g ae/kg, 10 g ae/kg to about 50 g ae/kg, 10 g ae/kg to about 40 g ae/kg, 10 g ae/kg to about 35 g ae/kg, 10 g ae/kg to about 30 g ae/kg, 10 g ae/kg to about 25 g ae/kg, or 15 g ae/kg to about 25 g ae/kg, with respect to the total herbicide delivery system.

The relative amounts of the solid carrier and the potassium salt of the herbicidal carboxylic acid used in the compositions described herein can be described by the weight ratio of the solid carrier to the potassium salt of the herbicidal carboxylic acid on an acid equivalent basis (ae basis). For example, the weight ratio of the solid carrier to the herbicidal carboxylic acid, on an ae basis, useful in the compositions described herein may range from about 10,000:1 to about 10:1, from about 5000:1 to about 10:1, from about 4000:1 to about 10:1, from about 3000:1 to about 10:1, from about 2000:1 to about 10:1, from about 1000:1 to about 10:1, from about 750:1 to about 10:1, from about 500:1 to about 10:1, from about 250:1 to about 10:1, from about 200:1 to about 10:1, from about 150:1 to about 10:1, from about 100:1 to about 10:1, from about 80:1 to about 10:1, from about 60:1 to about 10:1, from about 50:1 to about 10:1, from about 40:1 to about 10:1, or from about 30:1 to about 10:1. Additional weight ratios of the solid carrier to the herbicidal carboxylic acid, on an ae basis, may range from about 55:1 to about 40:1, from about 54:1 to about 41:1, from about 53:1 to about 42:1, from about 52:1 to about 43:1, from about 51:1 to about 44:1, from about 50:1 to about 45:1, or from about 49:1 to about 46:1. The weight ratio of the solid carrier to the herbicidal carboxylic acid, on an ae basis, may be about 500:1, 400:1, 300:1, 200:1, 100:1, 90:1, 80:1, 70:1, 60:1, 50:1, 40:1, 30:1, 20:1, or 10:1, and incremental values between these ratios. Additional weight ratios of the solid carrier to the herbicidal carboxylic acid, on an ae basis, may be about 55:1, 54:1, 53:1, 52:1, 51:1, 50:1, 49:1, 48:1, 47:1, 46:1, 45:1, 44:1, 43:1, 42:1, 41:1 or 40:1.

Also described is a method of improving the storage stability of a granular herbicidal composition containing a salt, e.g. an alkanolammonium salt such as triethanolammonium, of a herbicidal carboxylic acid, by using the potassium salt of the herbicidal carboxylic acid to coat the surface of the granules. Such granules are free flowing and do not cake during storage, and do not require the use of additional surface coating and drying processing steps in order to provide adequate storage stability properties.

Also described is a method of preparing the described herbicide delivery system which comprises:

(1) preparing an aqueous solution of the potassium salt of the herbicidal carboxylic acid;

(2) spraying the aqueous solution of the potassium salt of the herbicidal carboxylic acid onto the granular solid carrier; and (3) drying the resulting sprayed granular solid carrier to provide the described herbicide delivery system as non-sticky, free-flowing granules.

The described herbicide delivery system is produced in a simpler and more cost effective manner than some granular compositions containing amine salts of herbicidal carboxylic acids that are currently on the market. Such currently marketed compositions require an additional surface coating to prevent stickiness and improve flowability of the granules which require additional processing steps, drying energy and materials.

The described herbicide delivery system can be prepared with additional inert formulation ingredients such as, but not limited to: flow aids, surfactants, dyes, fertilizers, micronutrients, and many other additional ingredients providing functional utility.

Also described herein is a method of controlling undesirable vegetation comprising contacting the vegetation or the locus thereof with, or applying to the soil to control or prevent the emergence of the vegetation, a herbicidally effective amount of the herbicide delivery system described herein. The application of the herbicide delivery system to the undesirable vegetation may be done by broadcast or spot application. The herbicide delivery system which contains the potassium salt of picloram may be particularly useful for spot application for the control of brushweeds and broadleaf weeds, such as ragwort, nodding thistle, gorse, inkweed, broom, hemlock, docks, sweet brier and woolly nightshade, which can be found in range and pasture lands.

The herbicide delivery system described herein can also be used in conjunction with other pesticides such as, for example, herbicides, insecticides, fungicides, and plant growth regulators, and herbicide safeners, and various mixtures and combinations of these, and the like. These mixtures and combinations may be formulated together in a single granule composition, or they may be formulated as separate granule compositions, and applied together in one application or sequentially in separate applications. Such mixtures and combinations can be designed for application directly to weeds or their locus.

Herbicides that may be employed in conjunction with the herbicide delivery system described herein include, but are not limited to, 2,4-D, 2,4-DEB, 2,4-DEP, 2,3,6-TBA, acetochlor, acifluorfen, aclonifen, alachlor, allidochlor, alloxydim, alorac, ametridione, ametryn, amibuzin, amicarbazone, amidosulfuron, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clomazone, cloproxydim, cloransulam, CMA, copper sulfate, CPMF, CPPC, credazine, cresol, cumyluron, cyanatryn, cyanazine, cycloate, cyclosulfamuron, cycloxydim, cycluron, cyperquat, cyprazine, cyprazole, cypromid, daimuron, dalapon, dazomet, delachlor, desmedipham, desmetryn, di-allate, dichlobenil, dichloralurea, dichlormate, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoxasulfone, fenteracol, fentrazamide, fenuron, ferrous sulfate, flamprop, flamprop-M, flazasulfuron, florasulam, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, flurtamone, fluthiacet, fomesafen, foramsulfuron, fosamine, furyloxyfen, glufosinate, glufosinate-P, glyphosate, halauxifen, halosafen, halosulfuron, haloxydine, hexaflurate, hexazinone, imazamethabenz, imazamox, imazapic, imazapyr, imazaquin, imazethapyr, imazosulfuron, indanofan, indaziflam, iodobonil, iodosulfuron, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, karbutilate, ketospiradox, lactofen, lenacil, linuron, MAA, MAMA, medinoterb, mefenacet, mefluidide, mesoprazine, mesosulfuron, mesotrione, metam, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, rhodethanil, rimsulfuron, saflufenacil, S-metolachlor, sebuthylazine, secbumeton, sethoxydim, siduron, simazine, simeton, simetryn, SMA, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thiobencarb, tiocarbazil, tioclorim, topramezone, tralkoxydim, triafamone, triallate, triasulfuron, triaziflam, tribenuron, tricamba, triclopyr, tridiphane, trietazine, trifloxysulfuron, trifluralin, triflusulfuron, trifopsime, trihydroxytriazine, trimeturon, tripropindan, tritac, tritosulfuron, vernolate, and xylachlor.

Especially suitable combinations may comprise the compositions described herein used in conjunction with one or more of 2,4-D, cloransulam, diclosulam, florasulam, flumetsulam, halauxifen, isoxaben, metosulam, penoxsulam, pyroxsulam, tebuthiuron, and mixtures thereof.

The term herbicide is used herein to mean an active ingredient that kills, controls, or otherwise adversely modifies the growth of plants. A herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings, and established vegetation.

Herbicidal activity is exhibited by the compositions described herein when the compositions are applied directly to the plant or to the locus of the plant at any stage of growth or before planting or emergence. The effect observed depends upon the plant species to be controlled, the stage of growth of the plant, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action.

Application rates from about 5 to about 500 grams per square meter (gm/m$^2$) of the described herbicide delivery system may be used in broadcast applications around or on undesirable vegetation. Generally, such applications rates may be from about 10 to about 100 gm/m$^2$. The higher rates designated generally provide better control of a broad variety of undesirable vegetation some of which may be more herbicide tolerant or resistant. The lower rates are typically used for very sensitive vegetation, but may also give selective control and could, in certain cases, be employed in the locus of crops. Spot application rates to control individual plants may be from about 1 to about 100 grams of the described herbicide delivery system per plant.

Surface-active agents can be incorporated into the compositions described herein. The surface-active agents can be anionic, cationic, or nonionic in character and can be employed as, wetting agents, dispersing agents, or for other purposes. Surfactants conventionally used in the art of formulation and which may also be used in the compositions described herein are described, inter alia, in "McCutcheon's Detergents and Emulsifiers Annual", MC Publishing Corp., Ridgewood, N.J., 1998 and in "Encyclopedia of Surfactants", Vol. I-III, Chemical publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-C18 ethoxylate; alcohol-alkylene oxide addition products, such as tridecyl alcohol-C16 ethoxylate; soaps, such as sodium stearate; alkylnaphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, antimicrobial agents, and the like. The compositions of herbicidal carboxylic acids described herein may also contain other compatible components, for example, other herbicides, plant growth regulants, fungicides, insecticides, and the like.

The compositions described herein can be applied to weeds or their locus by the use of conventional ground or aerial granule applicators, and by other conventional means known to those skilled in the art.

The following Examples are presented to illustrate various aspects of the compositions described herein and should not be construed as limitations to the claims.

Example 1. Preparation of a Representative Sample of the Described Herbicide Delivery System—Sample 4

The herbicidal granule composition described herein was made in two steps using the ingredients listed in Table 1. In the first step, the preparation of the liquid aqueous phase containing the potassium salt of the herbicidal carboxylic acid was completed. In the second step, the liquid aqueous phase was sprayed onto the granular solid carrier and then the resulting granules were dried to provide the described herbicide granules.

(1) The liquid aqueous phase was prepared by adding a sufficient volume of water to a small mixing vessel under constant agitation. Then, KOH was added to and dissolved in the water. This creates some heat of dissolution that requires cooling the solution to room temperature. Once cooled, the active ingredients aminopyralid and picloram were added to the aqueous solution of KOH. The heat of reaction between the active ingredients and the KOH was then removed by cooling. Finally, the yellow tartrazine dye was added and the resulting solution was mixed until homogeneous.

(2) The limestone granules (chips; 16-40 mesh) were loaded into a Munsen mixer (similar to a concrete mixer and equipped with a hot air dryer) along with the surfactant and silica. This mixture was blended together for approximately 30 minutes and then the liquid aqueous phase was sprayed onto the limestone granule mixture as it was mixing. The hot air dryer was then turned on to commence the drying process which took about 2.5-3 hours. After drying was complete, moisture analysis showed the product was sufficiently dry (<0.75 wt % water).

Samples 1, 2, 3, 5, and 6 (Table 2) were prepared in a similar manner to Sample 4 except that triethanolamine (TEA) or triisopropanolamine (TIPA) were used in place of KOH for samples 1, 2, 3 and 6. Preparation of Sample 1 (Tordon™ 2G) also involved the additional steps of: (a) applying a finishing coating of Dantoin (by spraying in water) to the granules to prevent caking and, (b) heated drying.

TABLE 1

Composition of Pic-K/AP-K Herbicidal Granule - Sample 4

| Granule Composition - Sample 4 | Role | Active Ingredient (g ae/kg) | Amount (wt %) |
|---|---|---|---|
| aminopyralid potassium (AP-K) | active | 0.25 | 0.03 |
| picloram potassium (Pic-K) | active | 20.0 | 2.31 |
| sodium dodecylbenzene sulphonate | surfactant | | 0.50 |
| tartrazine | dye | | 0.05 |
| silica | anti-caking | | 1.36 |
| limestone granules (chips) | solid carrier | | 95.05 |
| water | inert | | 0.70 |
| Total | | | 100.00 |

Example 2. Stability Testing of Herbicidal Granule Compositions

Test Procedure:

Storage stability tests were run for 2 weeks at 47-70% relative humidity and 35-45° C. in open top glass beakers containing the test material compressed with a glass bottle filled with silica beads to obtain a pressure of 25 g/cm² (as per CIPAC MT 172). The stored samples were them examined in a flowability test. This test was designed to evaluate if a granular product will remain free flowing after storage under pressure. The test emulates storage conditions that promote caking in the package, an undesirable attribute of a granule formulation. From the flowability test results shown in Table 2, it was discovered that the potassium salt formulations (Samples 4 and 5) performed better than any of the picloram alkanolamine salt granules with (Sample 1) or without (Samples 2, 3, 6) a Dantoin coating. The picloram TIPA salt containing granules prepared without a Dantoin coating (Sample 6) became especially hard packed after storage.

TABLE 2

Flowability Results for Herbicide Granules Stored in an Elevated Humidity/Temperature Environment While Under Mechanical Pressure

| Sample ID # | Product or Active Ingredient Coated onto Granule | Dantoin Coating[1] | Amount of Caking | Flowability Results Standardized Movements to Initiate Flow[2] |
|---|---|---|---|---|
| 1 | Tordon ™ 2G[3] | Yes | Minimal | 3 |
| 2 | Picloram-TEA | No | Severe - granules hard packed | 14 |
| 3 | Picloram-TEA and 0.25 g/kg aminopyralid-TEA | No | Severe - granules hard packed | 13 |
| 4 | Picloram-K and 0.25 g/kg aminopyralid-K. | No | Minimal | 0 |
| 5 | Picloram-K | No | Minimal | 0 |
| 6 | Picloram -TIPA | No | Very severe - product did not leave the container | >25 |

[1]Dantoin is 5,5-dimethylimidazolidine-2,4-dione polymer with formaldehyde (Lonza);
[2]A standardized movement is a 1 cm drop onto a hard rubber sheet;
[3]Tordon ™ 2G contains 3.24 wt % of picloram triethanolamine (TEA) coated onto limestone granules which are then further coated with Dantoin (0.57 wt %, dry basis).

The present invention is not limited in scope by the embodiments disclosed herein which are intended as illustrations of a few aspects of the invention and any embodiments which are functionally equivalent are within the scope of this invention. Various modifications of the compositions and methods in addition to those shown and described herein will become apparent to those skilled in the art and are intended to fall within the scope of the appended claims. Further, while only certain representative combinations of the composition components and method steps disclosed herein are specifically discussed in the embodiments above, other combinations of the composition components and method steps will become apparent to those skilled in the art and also are intended to fall within the scope of the appended claims. Thus a combination of components or steps may be explicitly mentioned herein; however, other combinations of components and steps are included, even though not explicitly stated. The term "comprising" and variations thereof as used herein is used synonymously with the term "including" and variations thereof and are open, non-limiting terms.

What is claimed is:

1. A method of controlling undesirable vegetation comprising contacting the vegetation or the locus thereof with, or applying to the soil to control or prevent the emergence of the vegetation, a herbicidally effective amount of a herbicide delivery system comprising a solid carrier and a potassium salt of a herbicidal carboxylic acid coated onto the surface of the solid carrier, wherein the potassium salt of the herbicidal carboxylic acid is from about 0.1 gram acid equivalent per kilogram (g ae/kg) to about 100 g ae/kg of the total herbicide delivery system and the coated solid carrier is free flowing, non-sticky and does not cake during storage; wherein the solid carrier is limestone chips and the herbicidal carboxylic acid is selected from the group consisting of aminopyralid, aminocyclopyrachlor, clopyralid, dicamba and picloram and mixtures thereof.

2. The method of claim 1, wherein the herbicidal carboxylic acid is picloram.

3. The method of claim 1, further comprising a second herbicidal carboxylic acid.

4. The method of claim 3, wherein the second herbicidal carboxylic acid is aminopyralid.

5. The method of claim 1, wherein the herbicide delivery system is a granule or a pellet.

6. The method of claim 1, wherein the herbicide delivery system further comprises one or more inert ingredients.

7. The method of claim 1, wherein the herbicide delivery system further comprises a surfactant.

8. The method of claim 1, wherein the weight ratio of the solid carrier to the herbicidal carboxylic acid, on an acid equivalent basis, ranges from about 1000:1 to about 10:1.

9. The method of claim 1, wherein the weight ratio of the solid carrier to the herbicidal carboxylic acid, on an acid equivalent basis, ranges from about 55:1 to about 40:1.

10. A method of controlling undesirable vegetation comprising contacting the vegetation or the locus thereof with, or applying to the soil to control or prevent the emergence of the vegetation, a herbicidally effective amount of a herbicide delivery system comprising:
from about 925 g/kg to about 975 g/kg of a solid carrier comprising limestone chips, the limestone chips having a hard inert surface and an irregular shape; and
a mixture of herbicidal carboxylic acids comprising from about 10 g ae/kg to 30 g ae/kg of a picloram potassium salt and from about 0.1 g ae/kg to 1 g ae/kg of an aminopyralid potassium salt,
wherein the mixture of herbicidal carboxylic acids is coated onto the surface of the solid carrier and the coated solid carrier is free flowing, non-sticky and does not cake during storage.

11. A method according to claim 10, wherein greater than about 80% of the limestone chips have a particle size within a range from about 400 microns (μm) to about 1200 μm.

12. A method for improving the storage stability of a granular herbicidal composition containing a potassium salt of a herbicidal carboxylic acid, the method comprising coating a surface of a granular solid support with the potassium salt of the herbicidal carboxylic acid; wherein the solid granular support is limestone and the herbicidal carboxylic acid is selected from group consisting of aminopyralid, aminocyclopyrachlor, clopyralid, dicamba and picloram and mixtures thereof, and wherein the granular herbicidal composition is free flowing, non-sticky and does not cake during storage.

* * * * *